United States Patent [19]

Holst et al.

[11] 4,096,312

[45] Jun. 20, 1978

[54] DEPOSITION OF SWELLABLE, MODIFIED CELLULOSE ETHER ON WATER WET HYDROPHILIC SUBSTRATE

[75] Inventors: Arno Holst; Helmut Lask, both of Wiesbaden, Germany

[73] Assignee: Hoechst Aktiengesellschaft, Germany

[21] Appl. No.: 709,269

[22] Filed: Jul. 28, 1976

[30] Foreign Application Priority Data

Aug. 1, 1975 Germany ............................ 2534358

[51] Int. Cl.² ........................ B05D 1/12; B05D 5/04; B32B 23/02; B32B 29/02
[52] U.S. Cl. ..................................... 428/297; 118/73; 118/312; 128/290 R; 427/200; 427/324; 427/425; 428/326; 428/393
[58] Field of Search ................... 427/27, 32, 14, 185, 427/25, 200, 324–326, 506, 180, 189, 196, 391, 390 R, 392, 424, 425; 428/90, 326, 297, 393, 537, 532; 118/629–635, 73; 128/290 R, 290 P, DIG. 8; 239/3, 15; 162/192

[56] References Cited

U.S. PATENT DOCUMENTS

| 2,889,805 | 6/1959 | Freeder | 118/602 X |
|---|---|---|---|
| 3,589,364 | 6/1971 | Dean et al. | 162/146 X |
| 3,661,154 | 5/1972 | Torr | 128/284 |
| 3,723,413 | 3/1973 | Chatterjee et al. | 128/285 X |
| 3,901,236 | 8/1975 | Assarsson et al. | 128/290 R |

Primary Examiner—Morris Kaplan
Attorney, Agent, or Firm—James E. Bryan

[57] ABSTRACT

Process for the transformation of comminuted cellulose ether, which has been rendered at least largely water-insoluble by modification but is still highly swellable with water, into an easily workable material, comprising wetting a hydrophilic support web, applying the comminuted modified cellulose ether to the wetted web, and drying. This invention also relates to an apparatus for performing the process.

7 Claims, 5 Drawing Figures

DEPOSITION OF SWELLABLE, MODIFIED CELLULOSE ETHER ON WATER WET HYDROPHILIC SUBSTRATE

The present invention relates to a process, and the product thereof, for the transformation of comminuted and modified cellulose ether swellable with water, into a material that may be easily further processed and thus may be used without difficulty in the production of hygienic pads, napkins, bandages, tampons, and the like.

For the manufacture of such products, tissues or fleeces are used that can absorb aqueous liquids, in particular physiological body fluids such as blood or urine. Cellulose in the form of tissues, baize, cotton or paper is primarily used. For a long time certain substances have been added in order to increase the capacity of these articles to absorb aqueous liquids, for example moist potato flour, dextrin or gelatin have been applied to the cellulose material and dried (German Patent No. 489,309).

Recently it has become known to use cellulose ethers, which have been rendered at least largely water-insoluble by modification, for increasing the water absorption capacity of such materials. Modification is carried out with the cellulose material before, during, or after the etherification of the cellulose. The etherification agent and the degree of etherification are chosen in such a manner that without modification a cellulose ether essentially soluble in water at 20° C would be produced. By means of the modification the cellulose ether is rendered at least largely water-insoluble but is highly swellable with water. Processes for the manufacture of such modified cellulose ethers are described in U.S. Pat. Nos. 3,589,364, and 3,723,413. The cellulose ethers modified in this manner maintain their fibrous structure. This is done on purpose, in order to render possible further processing of the modified cellulose ethers obtained, either on their own or mixed with fibers or other cellulose material to form fiber fleeces, baize, bandages, cushions, napkins or tampons. Thus the production of modified cellulose ethers and their further processing into useful objects was limited and further development in this technical field was hindered.

It is the object of the present invention to provide a process in which comminuted modified cellulose ethers swellable with water are transformed, by a method other than fleece-forming or baize-forming, into an easily workable material that may be conveniently used especially in the production of bandage material, hygienic pads, napkins, tampons and the like. This object is achieved by a process in which a comminuted and modified cellulose ether is attached to a hydrophilic support, i.e. a web of hydrophilic material, at least one surface of the web is wetted with water, the comminuted modified cellulose ether is applied to this surface, and then the web is dried.

The modified cellulose ethers suitable for the process are not only those havng a fibrous structure, but may be others that may have any form as long as they are comminuted and pourable. Cellulose ethers in this state will hereinafter be called powder, irrespective of whether the powder particles are fibrous, crumbs of irregular shape, or otherwise comminuted. The size of the powder particles is of no decisive importance for the realization of the invention. It may be 1 mm and more, in practice it is mainly in the range of from 0.02 to 0.5 mm. Cellulose ethers are preferably used that are modified by cross-linking according to the process described in German Offenlegungsschrift No. 2,357,079, or that are modified according to German Offenlegungsschrift No. 2,358,150. They have a high water absorption capacity and water retention value. Modified cellulose ethers usable within the scope of the invention are also, for example, ammonium salts of cellulose glycol acids modified by means of heat according to the process described in German Patent No. 839,492, or the gel-forming cellulose ether modifications obtained by heating alkali salts of cellulose glycol acid according to the process disclosed in U.S. Pat. No. 2,639,239.

These modifications of cellulose ethers lead to products having an acceptable water absorption capacity even if the modified cellulose ether still contains water-soluble parts. Thus in practice cellulose ethers are often not modified to form completely water-insoluble products, and in most cases the water-soluble parts are not removed from the modified cellulose ethers. The water-soluble portion may consist of those parts of cellulose ether which were not modified at all or of those parts which were not modified enough to become a water-insoluble product. As a matter of fact, a water-soluble portion of at least 15 percent by weight is advantageous in most cases, because it improves adhesion of the particles of modified cellulose ether to the hydrophilic web. However, the water-soluble portion should not exceed approximately 50 percent by weight.

The hydrophilic web serving as a support preferably is cellulose. In most cases it is an absorbent paper or cellulose tissue, such as mull. For many purposes a suitable support is a film web composed of regenerated cellulose, i.e. cellophane. The easiest way of wetting the surface of the support is to briefly dip the web into water and then squeeze it to the desired degree of moisture. The swellable powder is applied, for example, by strewing it onto the moist surface of the web, or in a vortex chamber.

In the process only those powder particles adhere to the support that come into direct contact with the moist surface. The maximum amount of powder particles adhering to the surface is determined by the number of particles that can lie closely side by side in one layer on the moist surface of the support. This highest density will be used in those cases in which it is important to obtain a maximum water absorption capacity per unit area. In this case more than the necessary amount of powder may be applied to the moist surface, since the excess powder can easily be removed, for example by blowing, and then can be reused. On the other hand, if maximum use is to be made of the water-absorption capacity of the absorbent powder, it is useful not to apply to the moist support more than 50 percent by weight of the maximum amount of powder that can be applied according to the process of the invention. If the water-absorbing powder is to adhere only to parts of the surface, for example if uncoated marginal areas or a coating according to a different pattern are required, it is useful to wet the surface of the web only in parts, i.e. according to the pattern desired, e.g. by spraying it with water accordng to the pattern. The pattern desired also may be obtained by applying the powder to parts of the moist surface of the web. In this case the web surface or the entire web may be wetted, e.g. by dipping it into water.

The process according to the invention will now be further described, by way of example only, with reference to the accompanying drawings, in which:

FIG. 1 is a schematic view of an apparatus for performing the process,

FIG. 2 and FIG. 3 explain the guidance of the web in the apparatus of FIG. 1,

Figure 1:
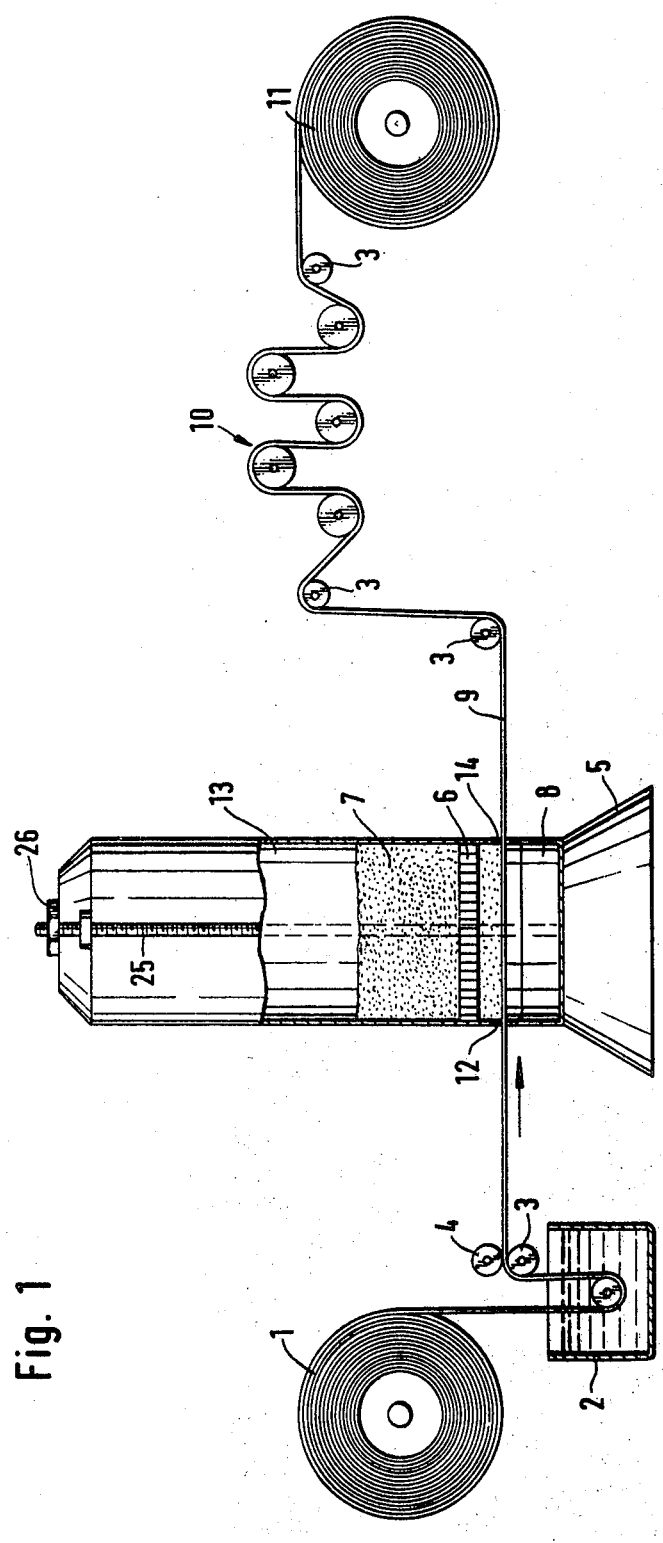
Figure 4:
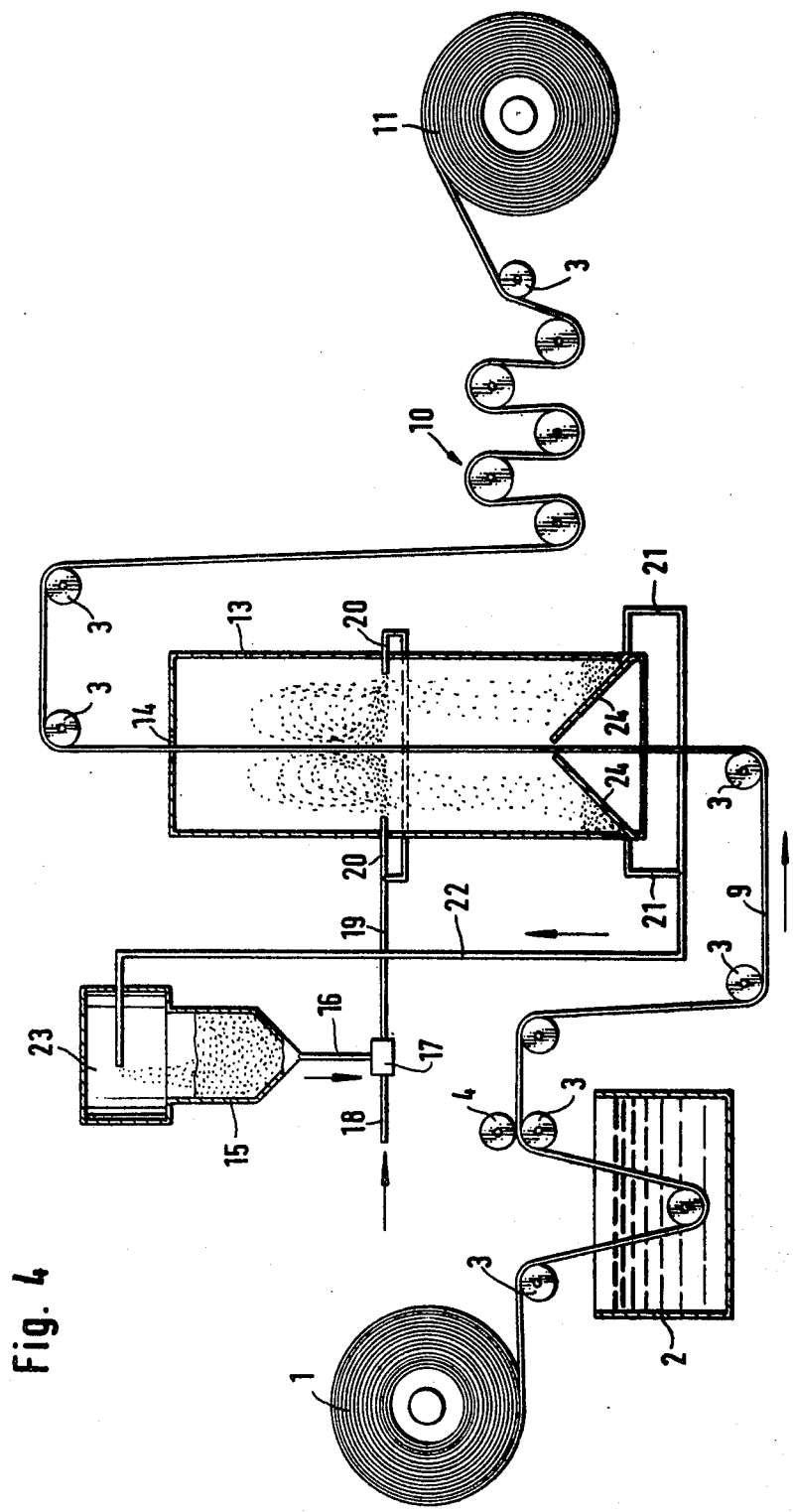
FIG. 4 is a schematic view of another apparatus for performing the process.

If the apparatuses shown in FIGS. 1 and 4 are used, the web 9 to be coated is rolled up on a supply roll 1. It is unrolled, passes through a tray 2 filled with water and is subsequently guided around a deviating roller 3, where it is squeezed by a squeegee roller 4 to the water content desired. The web 9 then enters a powdering chamber 13 through an input slot 12 and leaves it, after powdering, through an output slot 14. Before entering the powdering chamber 13 the web 9 may be deviated by further deviating rollers 3 (FIG. 4). After leaving the powdering chamber 13 the powdered web 9 passes further deviating rollers 3 and reaches a drying device 10 composed of drying drums around which the web is guided, before it reaches, via another deviating roller 3, a winding up device 11 where it is wound up to form a wound roll.

In the apparatus shown in FIG. 1 the powdering chamber 13 is that part of a vibrating screen device which can be taken off the vibration device 5 and can be attached to it by means of two threaded rods 25 and two screws 26. Whereas in use as a screen device, the chamber 13 usually houses a set of screens arranged one above the other, in the present case it is only one screen 6. Above the screen there is a supply 7 of the powder to be used. This powder is preferably sifted in such a manner that particles can pass through the meshes of the screen. Spacers (not shown in FIGS. 1 and 4) maintain the powdering chamber 13 at such a distance from the lower part that the input and output slots 12 and 14 are produced. Due to the vibration of the screen 6, powder falls onto the moist web 9 that is transported throgh the powdering chamber 13. By the passing speed of the web 9 and the way in which the screen is vibrated the powdering of the web surface can be controlled, so as to apply more or less powder to it, as desired. If more powder is applied to the moist web surface than can adhere to it, the excess powder is removed from the web, is collected and reused in another powdering process. The portion of the powder which falls beside the web 9 in the powdering chamber is collected in a collecting vessel 8.

Figure 2:
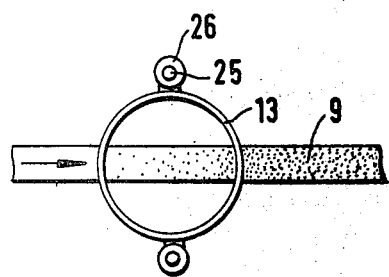

The web shown in FIGS. 1 and 2 is powdered only on one side, i.e. its upper side.

Figure 3:
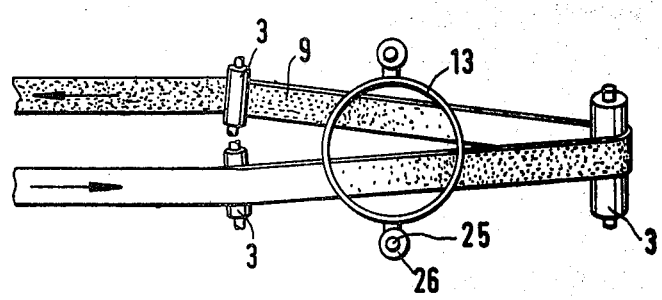

If both sides are to be powdered, the web 9 is guided as shown schematically in FIG. 3: After leaving the powdering chamber 13 it is deviated by a deviating roller 3 in such a manner that its lower surface becomes its upper surface and it passes back at a small angle to its former direction of transport, so that it passes through the powdering chamber 13 in an opposite direction, the part of the web 9 moving forward and the part moving backward not being superposed. The drying device 10 and the wind-up roll 11 are then arranged at the input side of the apparatus. The web 9 is deviated into its opposite direction only after having passed the drying device 10 after powdering of one of its surfaces. After powdering the other surface this surface is dried in a second drying process either in a second drying device or in the same drying device that is used for the first drying, after guiding the web 9 back accordingly.

In the apparatus shown in FIG. 4 the powdering chamber 13 is a vortex chamber. A supply container 15 for the powder is arranged outside the vortex chamber. From there the powder passes through a powder conduit 16 into an ejector 17, to which compressed air is fed through an air conduit 18. The powder-air mixture is guided, through a branching mixture conduit 19, to two spray nozzles 20 which blow the mixture into the powdering chamber 13 while forming a vortex. The moist web 9 that is guided through the chamber 13 from bottom to top is covered on both sides with the whirled-up powder. The unused powder is taken away by the air blown into the chamber. It leaves the vortex chamber via two output conduits 21, which merge into one collecting conduit 22, through which the powder-containing air reaches a settling chamber 23, from which the settling powder falls into the supply container 15. The air blown into the vortex chamber 13 and the settling powder are guided, by guiding plates 24, into the discharge conduits 21.

The invention will be further illustrated by reference to the following specific examples.

EXAMPLE 1

A web of creped paper having a weight of 48.32 g/m² is guided through water, as shown in FIG. 1, and after removing the water adhering thereto, it is passed through a laboratory vibrating screen device. The modified carboxymethyl cellulose to be applied, which is largely water-insoluble and has a water absorption capacity of 3800 g/100g, is applied though an 0.2 mm screen, so that after drying the weight of the paper is increased by 42 g/m². Before powdering, the creped paper has an absorption capacity of 336 g per 100 g. Due to the powdering, its water absorption capacity increases to 2012 g per 100 g of powdered paper. Its absorption capacity for synthetic urine solution increases from 70 to 145 g and for synthetic blood solution from 71 to 127 g per 100 g of powdered paper (synthetic urine solution and synthetic blood solution are aqueous solutions the physical properties of which are very similar to human urine and blood).

EXAMPLE 2

A tissue paper web having a weight of 23.6 g/m² is wetted and powdered as described in Example 1. After drying, its weight has increased by 52 g/m². The absorption capacity for water of the powdered tissue paper increases from 650 to 3000 ml per 100 g.

EXAMPLE 3

A tissue paper web having a weight of 31.5 g/m² is wetted and subsequently powdered on both surfaces as shown in FIG. 1 combined with FIG. 3. The moist web is deviated within the powdering chamber and dried only after the second powdering. The weight increase after drying is 4.7 g/m², and the absorption capacity increases from 800 to 1440 g of water per 100 g of paper.

EXAMPLE 4

A web of regenerated cellulose having a weight of 48 g/m² is soaked with a 4 percent by weight aqueous glycerin solution, liquid adhering to it is removed, and one surface of the web is subsequently powdered with a swellable cellulose ether in the powdering device shown in Example 1. After drying its weight is 80 g/m², and its absorption capacity has increased from 200 to 2460 ml of water per 100 g.

EXAMPLE 5

After being wetted, a medical mull bandage having a width of 8 cm is powdered on one side with a cellulose ether, which has a blood retention value of 980 ml/100 g, and after drying the weight of the bandage has increased by 20 percent by weight. The blood retention increases from 763 to 1298 ml per 100 g of mull bandage.

EXAMPLE 6

A tissue paper web having a weight of 31.5 g per $m^2$ is powdered on one side, as described in Example 1, with the modified cellulose ether the water absorption capacity of which is 3800 ml, and its absorption capacity for a 1 percent by weight salt solution is 2000 ml per 100 g. The powdering density is increased to its maximum, i.e. 16 g/$m^2$. The following results were obtained:

| Material | Absorption capacity per 100 g of material | |
|---|---|---|
| | ml of 1% by weight NaCl solution | ml of water |
| tissue paper without powder | 420 | 420 |
| with 1.6 g/$m^2$ of powder | 600 | 750 |
| with 3.2 g/$m^2$ of powder | 800 | 1440 |
| with 8.0 g/$m^2$ of powder | 950 | 1580 |
| with 16 g/$m^2$ of powder | 1100 | 2000 |
| powder | 2000 | 3800 |

Figure 5:
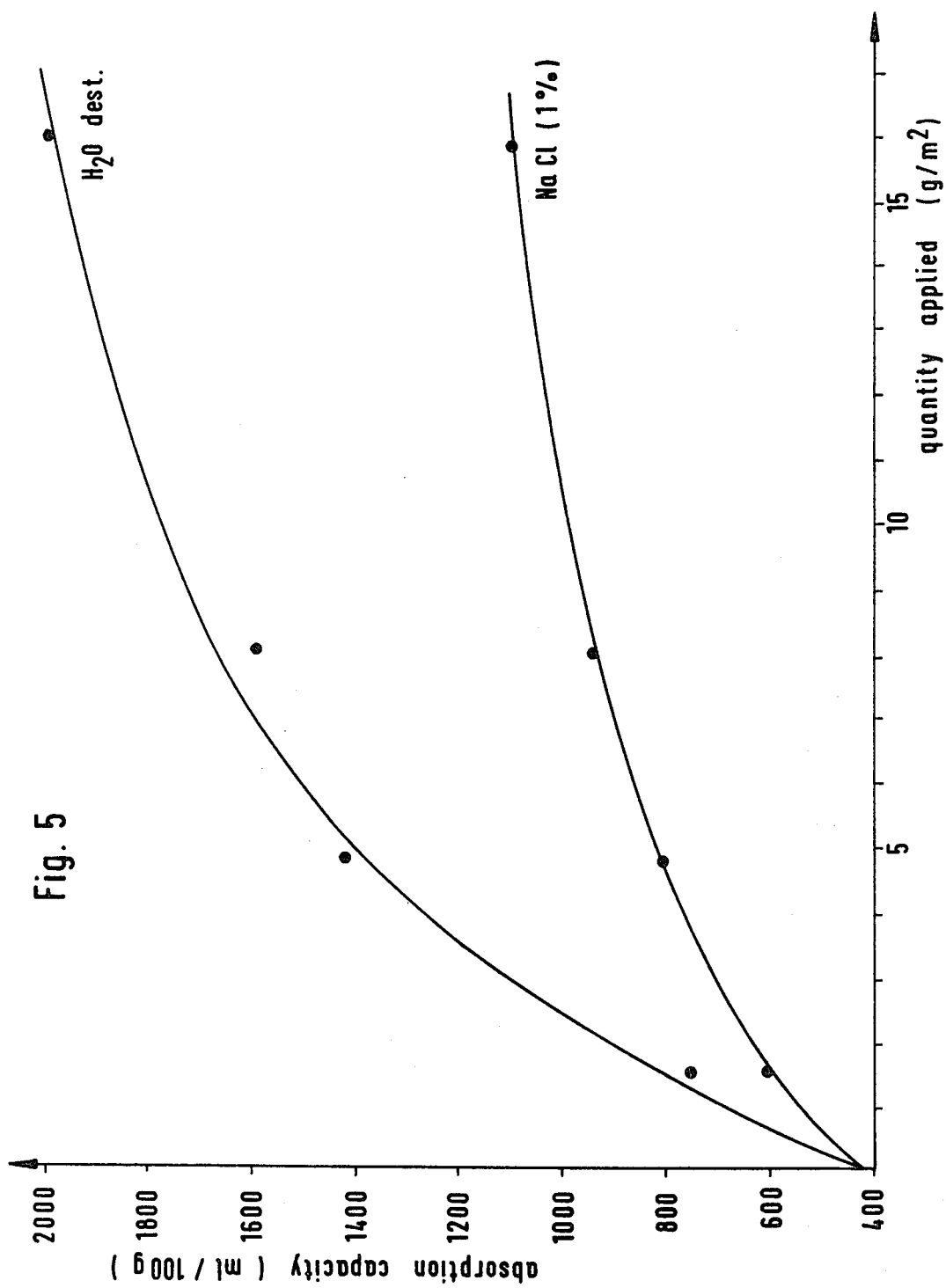
FIG. 5 is a diagram which explains the effect of incomplete covering of the web with the powder.

The results are shown in the diagram of FIG. 5. It can be seen that the absorption capacity (ordinate), based on an increase in the amount of powder (abscissa) by 1 g, increases the more the less powder has been used on the whole and that when the maximum powder application of 16 g/$m^2$ is approached, the absorption capacity increases only insignificantly with an increase in the powder quantity by 1 g. It also can be seen that with half of the maximum powdering, i.e. 8 g/$m^2$, an absorption capacity towards distilled water of 1580 ml per 100 g of web material is obtained, and an absorption capacity for a 1 percent by weight salt solution of 950 ml per 100 g of web material. Thus the maximum values of 2000 g and 1100 g per 100 g of web material are already approached.

It will be obvious to those skilled in the art that many modifications may be made within the scope of the present invention without departing from the spirit thereof, and the invention includes all such modifications.

What is claimed is:

1. A process for the transformation of comminuted cellulose ether, which has been rendered at least largely water-insoluble by modification but is still highly swellable with water, into an easily workable material, comprising wetting at least one surface of a hydrophilic support web, applying the comminuted modified cellulose ether to the wetted web, and drying.

2. A process according to claim 1 in which the comminuted modified cellulose ether is more than 15 percent by weight, but less than 50 percent by weight, water-soluble.

3. A process according to claim 1 in which the hydrophilic web is composed of cellulose.

4. A process according to claim 3 in which the web is composed of paper, tissue, or regenerated cellulose.

5. A process according to claim 1 in which only parts of the surface of the web are wetted with water.

6. A process according to clam 1 in which the wetted surface is incompletely covered with the comminuted modified cellulose ether.

7. A coated web composed of a hydrophilic material and produced according to the process of claim 1.

* * * * *